(12) United States Patent
Refouvelet

(10) Patent No.: US 9,440,940 B2
(45) Date of Patent: Sep. 13, 2016

(54) METHODS FOR SYNTHESIS OF PSORALEN DERIVATIVES

(71) Applicant: MACOPHARMA, S.A.S., Mouvaux (FR)

(72) Inventor: Bernard Refouvelet, Besancon (FR)

(73) Assignee: Macopharma, S.A.S., Mouvaux (FR)

( * ) Notice: Subject to any disclaimer, the term of this patent is extended or adjusted under 35 U.S.C. 154(b) by 0 days.

(21) Appl. No.: 14/660,514

(22) Filed: Mar. 17, 2015

(65) Prior Publication Data

US 2015/0266845 A1    Sep. 24, 2015

(30) Foreign Application Priority Data

Mar. 18, 2014  (FR) ..................... 14 00658

(51) Int. Cl.
*C07D 493/00* (2006.01)
*C07D 311/16* (2006.01)
*C07D 493/04* (2006.01)

(52) U.S. Cl.
CPC ........... *C07D 311/16* (2013.01); *C07D 493/04* (2013.01)

(58) Field of Classification Search
CPC .................................................. C07D 493/04
USPC ....................................... 549/282
See application file for complete search history.

(56) References Cited

U.S. PATENT DOCUMENTS 8,466,283 B2 * 6/2013 Hentemann et al. ......... 544/250

OTHER PUBLICATIONS

Yoshida, Synthesis, (12), 1026-7; 1986.*
Poshiya International Journal of Pharmacy and Technology, 3(3), 3048-3059; 2011.*
Traven, Valery F., Arkivoc 1(4), 523-562; 2000.*
Wada Organic & Biomolecular Chemistry, 9(13), 4959-4976; 2011.*
Traven, Valery F., "Dihydrofurocoumarinones—new useful intermediates for substituted and condensed furocoumarins", ARKIVOC 2000 (iv) General Papers, Sep. 29, 2000, pp. 523-562.
Gonzalez-Gomez, J.C. et al., "Synthesis and convenient functionalisation of pyridazinofurocoumarins; nitrogenated isoesters of potent DNA inhibitors", Tetrahedron, vol. 59, No. 41 (2003), pp. 8171-8176.
Yoshida, Yukio et al., "A Convenient Synthesis of Coumarins by Denitro-cyclization", Synthesis, vol. 1986, No. 12 (1986), pp. 1026-1027.
DeLuca, Laura et al., "HIV-1 integrase strand-transfer inhibitors: Design, synthesis and molecular modeling investigation", European Journal of Medicinal Chemistry, vol. 46, No. 2 (2011), pp. 756-764.
Nore, Pentti et al., "A new synthesis of methoxalen", Journal of Heterocyclic Chemistry, vol. 17, No. 5 (1980), pp. 985-987.

* cited by examiner

*Primary Examiner* — Nizal Chandrakumar
(74) *Attorney, Agent, or Firm* — Baker Botts L.L.P.

(57) ABSTRACT

Methods for the synthesis of psoralen derivatives are provided. In one embodiment, the method may include acetylating a compound of formula (II) to form a compound of formula (III), subjecting the compound of formula (III) to a Fries rearrangement to form a compound of formula (IV), and subjecting the compound of formula (IV) to cyclization, reduction and aromatization, to form a compound having the following formula (I):

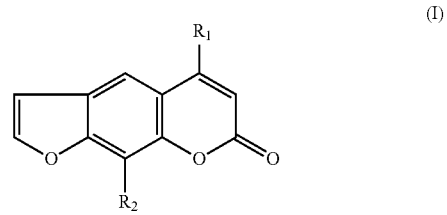

19 Claims, 2 Drawing Sheets

METHODS FOR SYNTHESIS OF PSORALEN DERIVATIVES

CROSS REFERENCE TO RELATED APPLICATIONS

This application claims the benefit of French application No. 1400658, filed Mar. 18, 2014, the entire disclosure of which is hereby incorporated by reference.

BACKGROUND

The present disclosure generally relates to the field of extracorporeal photochemotherapy.

Extracorporeal photochemotherapy is an autologous cell therapy technique that consists of obtaining a cell suspension rich in mononuclear cells (apheresis or constitution of a buffy coat in line), adding to it a photosensitizing agent such as 8-methoxypsoralen (8-MOP), and then exposing the suspension to UVA radiation. The cells thus modified are then reinjected into the patient.

Over the past few years, extracorporeal photochemotherapy has become an alternative treatment for various diseases, such as cutaneous T-cell lymphoma, autoimmune diseases, and the acute form and steroid-recalcitrant form of graft-versus-host disease.

The 8-MOP used for extracorporeal photochemotherapy is a molecule that is part of the furocoumarin or psoralen family. In particular, it is the active substance from the *Ammi majus* plant. 8-MOP can be prepared by extraction and isolation from such a plant using organic solvents. But, residual traces of these solvents, that may present a certain toxicity, are found in the final product.

Synthetic processes for obtaining furocoumarins also exist. For example, U.S. Pat. No. 4,130,568 proposes a process for preparing 8-methoxypsoralen from 6-allyl-7-hydroxy-8-methoxycoumarin. First, this starting product undergoes oxidative cyclization in the presence of a catalyst to form 4',5'-dihydro-furocoumarin, which is then processed with a strong acid to cleave the hydroxy group at position 5' and induce dehydrogenation to form 8-methoxypsoralen. The disadvantage of this synthesis is the difficulty obtaining the starting product.

U.S. Pat. No. 4,147,703 also proposes a synthetic process for obtaining 8-methoxypsoralen from 6-hydroxy-7-methoxy-1-benzofuran-2(3H)one (A) by reacting it with hydrogen and a noble metal; (B) by reacting the product obtained in step (A) with a mixture of zinc cyanide and hydrochloric acid; (C) by reacting the product obtained in step (B) with dichlorodicyanoquinone in an inert solvent; (D) by reacting the product obtained in step (C) with ethyl cyanoacetate in a polar solvent; and (E) by decarboxylating the product obtained in step (D) to obtain 8-methoxypsoralen.

A process in three steps for preparing furocoumarins substituted in position 8 from 7-hydroxycoumarin is also described in FR Patent Application No. 2,404,641. The process includes (a) reacting 7-hydroxycoumarin with a halogeno-acetal so as to form a coumarin acetal; (b) transforming the coumarin acetal into aldehyde by heating in a diluted solution; and (c) cyclizing the aldehyde in furocoumarin by heating in an alkaline solution. A global yield of 50% is claimed, which remains relatively low.

In the publication Traven, V. F. (2000), Dihydrofurocoumarinones-new useful intermediates for substituted and condensed furocoumarins, Arkivoc, 4, 523-562, furocoumarinone derivatives are obtained from 7-chloroacetoxycoumarin derivatives by an unusual Fries rearrangement carried out at high temperature. A reduction/dehydration or acetylation step is then proposed to obtain psoralen derivatives. However, this synthesis produces many by-products.

SUMMARY

The present disclosure generally relates to the field of extracorporeal photochemotherapy. More specifically, the present disclosure relates to methods for the synthesis of a psoralen derivative substituted in position 4 and 8 from a 7-hydroxycoumarin derivative substituted in position 4 and 8.

In one embodiment, the present disclosure provides a method comprising: (a) acetylating a compound having the following formula (II):

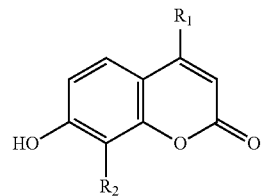

wherein acetylating the compound of formula (II) forms a compound having the following formula (III):

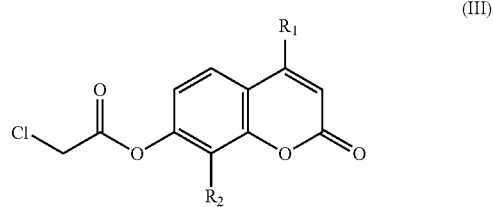

(b) subjecting the compound of formula (III) from step (a) to a Fries rearrangement, wherein the Fries rearrangement forms a compound having the following formula (IV):

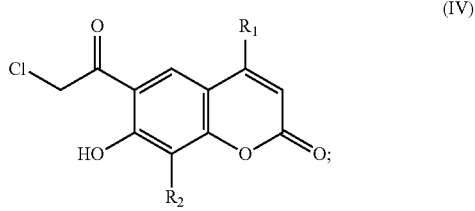

(c) subjecting the compound of formula (IV) obtained in step (b) to cyclization, reduction and aromatization, to form a compound having the following formula (I):

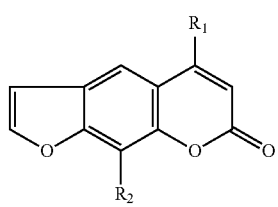

(I)

wherein $R_1$ in formulas (I)-(IV) is selected from the group consisting of a hydrogen atom; a linear C1-C6 alkyl group; and a branched C1-C6 alkyl group, and wherein $R_2$ in formulas (I)-(IV) is selected from the group consisting of a hydrogen atom; a linear C1-C6 alkyl group; a branched C1-C6 alkyl group; a linear C1-C6 alkoxy group; and a branched C1-C6 alkoxy group.

Further objects and advantages will become clear from the following description.

DRAWINGS

Some specific example embodiments of the disclosure may be understood by referring, in part, to the following description and the accompanying drawings.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to the field of extracorporeal photochemotherapy. More specifically, the present disclosure relates to methods for the synthesis of a psoralen derivative substituted in position 4 and 8 from a 7-hydroxycoumarin derivative substituted in position 4 and 8.

One obstacle to the processes described in the prior art are that they provide a relatively low yield and often require steps that are laborious to implement, such as steps performed at high temperatures. Certain embodiments of the present disclosure may avoid these issues.

The present disclosure provides methods for synthesis that, in certain embodiments, are easily industrialized under good manufacturing practices, enabling a good yield but also a high purity of the final product to be obtained.

The present disclosure relates to methods for the synthesis of a compound having the following formula (I):

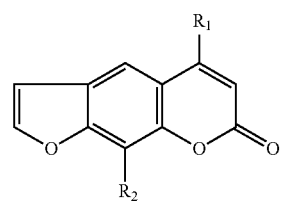

(I)

wherein $R_1$ is selected from the group consisting of a hydrogen atom; a linear C1-C6 alkyl group; and a branched C1-C6 alkyl group, and wherein $R_2$ is selected from the group consisting of a hydrogen atom, a linear C1-C6 alkyl group, a branched C1-C6 alkyl group, a linear C1-C6 alkoxy group, and a branched C1-C6 alkoxy group.

In certain embodiments, the compound of formula (I) may be a psoralen derivative, wherein $R_1$ is a hydrogen atom and $R_2$ is a methoxy group. This derivative is 8-methoxypsoralen (8-MOP).

In one embodiment, the method according to the present disclosure comprises the following successive steps: (a) acetylating a compound having the following formula (II):

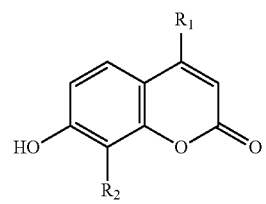

(II)

wherein $R_1$ is selected from the group consisting of a hydrogen atom; a linear C1-C6 alkyl group; and a branched C1-C6 alkyl group, and wherein $R_2$ is selected from the group consisting of a hydrogen atom, a linear C1-C6 alkyl group, a branched C1-C6 alkyl group, a linear C1-C6 alkoxy group, and a branched C1-C6 alkoxy group; and wherein step (a) forms a compound having the following formula (III):

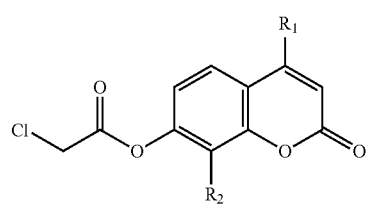

Figure 1:
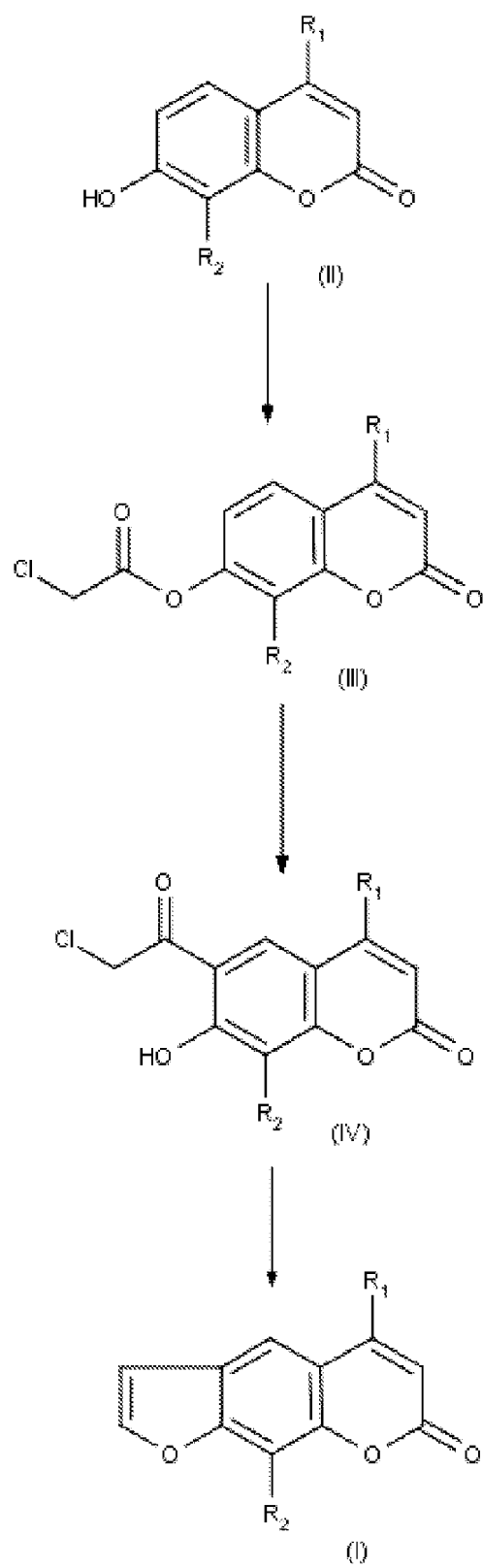
FIG. 1 is a diagram illustrating the synthesis of a compound of formula (I) from a compound of formula (II).

(III)

wherein $R_1$ and $R_2$ are as described above. In step (b), the compound of formula (III) obtained in step (a) is subjected to a Fries rearrangement to form a compound having the following formula (IV):

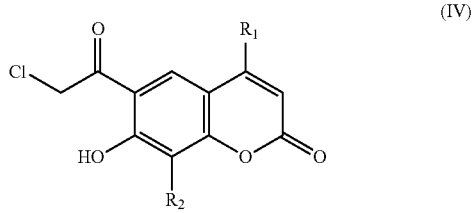

wherein $R_1$ and $R_2$ are as described above. In step (c), cyclization, reduction and aromatization of the compound of formula (IV) occurs, to form the compound of formula (I). FIG. 1 is a diagram illustrating one embodiment of the present disclosure for the synthesis of a compound of formula (I).

In certain embodiments, the methods of the present disclosure may result in the formation a compound of formula (I), wherein $R_1$ is a hydrogen atom and $R_2$ represents a methoxy group. In certain embodiments, the method may result in the formation of a compound of formula (I) wherein $R_2$ represents a methoxy group.

In certain embodiments, the methods of the present disclosure may be used to prepare 8-MOP, one example of a compound of formula (I) wherein $R_1$ is a hydrogen atom and $R_2$ is a methoxy group, from hydrangetin, one example of a compound of formula (II), wherein $R_1$ is a hydrogen atom and $R_2$ is a methoxy group. Hydrangetin is one example of a commercially available compound of formula (II). One advantage of the methods of the present disclosure is that the combination of hydrangetin as the starting product and the use of an acetylation reaction and Fries rearrangement enables an 8-MOP compound to be obtained in only three steps, under industrializable conditions and by respecting good manufacturing practices (GMP).

In one embodiment, step (a) of the method according to the present disclosure is an acetylation step performed by any known means. In particular, acetylation step (a) is performed using 2-chloroacetyl chloride in the presence of a base. This acetylation step is advantageously conducted at ambient temperature in order to prevent the formation of by-products. Unless indicated otherwise, it is understood that the temperatures indicated in the present disclosure are the temperatures of the reaction mixtures.

In one embodiment, step (b) of the method according to the present disclosure is a Fries rearrangement. The Fries rearrangement may be performed at a temperature of from about 90° C. to about 120° C. In certain embodiments, the Fries rearrangement may be performed at a temperature of from about 95° C. to about 110° C. In certain embodiments, the Fries rearrangement may be performed at a temperature of about 100° C. According to the methods of the present disclosure, a reaction temperature in this range enables a compound of formula (IV) with a yield of over 80% to be selectively obtained from a compound of formula (III) substituted in position 8. In certain embodiments, the substitution in position 8 may be by a methoxy group. Heating to a higher temperature leads to the formation of degradation products and by-products.

The compound of formula (IV) is then cyclized, reduced and aromatized to lead to the compound of formula (I). The cyclization of step (c) is generally performed by heating in basic medium. In certain embodiments, cyclization is performed by heating the compound of formula (IV) in the presence of an alkali carbonate. One example of an alkali carbonate that may be used is sodium carbonate. In certain embodiments, the reduction of step (c) is performed using an alkaline borohydride. One of example of an alkaline borohydride that may be used is sodium borohydride. The reaction medium may be neutralized in acid medium, for example by sulfuric acid, and that enables the product to be aromatized.

Carrying out Fries rearrangement step (b) at the determined temperature controls the selective formation of the compound of formula (IV), and therefore controls the purity of the final product of formula (I), since the cyclization/reduction/aromatization step (c) is also fully controlled.

In order for the synthesis of the compound of formula (I) to satisfy GMP requirements, finding a reliable source of a compound of starting formula (II) is generally necessary. In the absence of a reliable source of a compound of formula (II), which in certain embodiments may be hydrangetin, the present disclosure, in another embodiment, also provides methods for the synthesis of a compound of formula (II) from a starting product that can be obtained from a reliable source.

In another embodiment of the present disclosure, a compound of formula (II), as depicted above and used in step (a), is prepared by a method having only four steps. According to this embodiment, a method for the synthesis of the compound of formula (I) comprises the preliminary synthesis of a compound of formula (II) from a compound having the following formula (V):

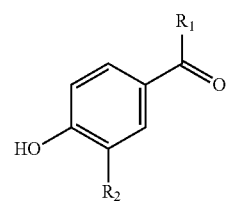

wherein $R_1$ is selected from the group consisting of a hydrogen atom; a linear C1-C6 alkyl group; and a branched C1-C6 alkyl group, and wherein $R_2$ is selected from the group consisting of a hydrogen atom, a linear C1-C6 alkyl group, a branched C1-C6 alkyl group, a linear C1-C6 alkoxy group, and a branched C1-C6 alkoxy group.

In certain embodiments, the compound of formula (V) is a 4-hydroxybenzaldehyde, wherein $R_1$ is a hydrogen atom and $R_2$ is a methoxy group. Formula (V) having these properties is referred to as vanillin. Vanillin is a product that is generally commercially available from reliable manufacturers.

In certain embodiments, the methods of the present disclosure comprise the following successive steps for the synthesis of the compound of formula (II): (a) acetylating a compound of formula (V), as shown above, to form a compound having the following formula (VI):

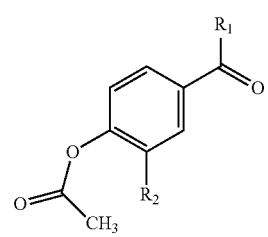

wherein R₁ is selected from the group consisting of a hydrogen atom; a linear C1-C6 alkyl group; and a branched C1-C6 alkyl group, and wherein R₂ is selected from the group consisting of a hydrogen atom, a linear C1-C6 alkyl group, a branched C1-C6 alkyl group, a linear C1-C6 alkoxy group, and a branched C1-C6 alkoxy group; (b) nitrating the compound of formula (VI) obtained in step (a), to form a compound having the following formula (VII):

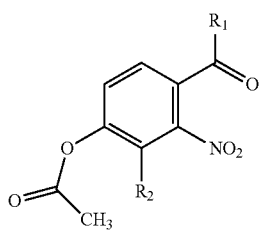

(VII)

wherein R₁ is selected from the group consisting of a hydrogen atom; a linear C1-C6 alkyl group; and a branched C1-C6 alkyl group, and wherein R₂ is selected from the group consisting of a hydrogen atom, a linear C1-C6 alkyl group, a branched C1-C6 alkyl group, a linear C1-C6 alkoxy group, and a branched C1-C6 alkoxy group; (c) hydrolyzing the compound of formula (VII) obtained in step (b) to form a compound having the following formula (VIII):

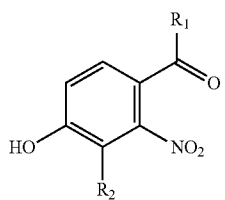

(VIII)

wherein R₁ is selected from the group consisting of a hydrogen atom; a linear C1-C6 alkyl group; and a branched C1-C6 alkyl group, and wherein R₂ is selected from the group consisting of a hydrogen atom, a linear C1-C6 alkyl group, a branched C1-C6 alkyl group, a linear C1-C6 alkoxy group, and a branched C1-C6 alkoxy group; (d) subjecting the compound of formula (VIII) obtained in step (c) to Knoevenagel condensation to form a compound having following formula (IX):

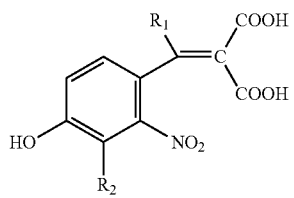

(IX)

wherein R₁ is selected from the group consisting of a hydrogen atom; a linear C1-C6 alkyl group; and a branched C1-C6 alkyl group, and wherein R₂ is selected from the group consisting of a hydrogen atom, a linear C1-C6 alkyl group, a branched C1-C6 alkyl group, a linear C1-C6 alkoxy group, and a branched C1-C6 alkoxy group; (e) cyclizing the compound of formula (IX) obtained in step (d) to obtain a compound having the following formula (II):

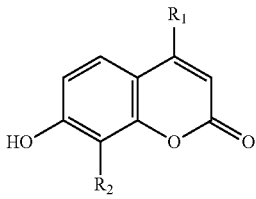

Figure 2:
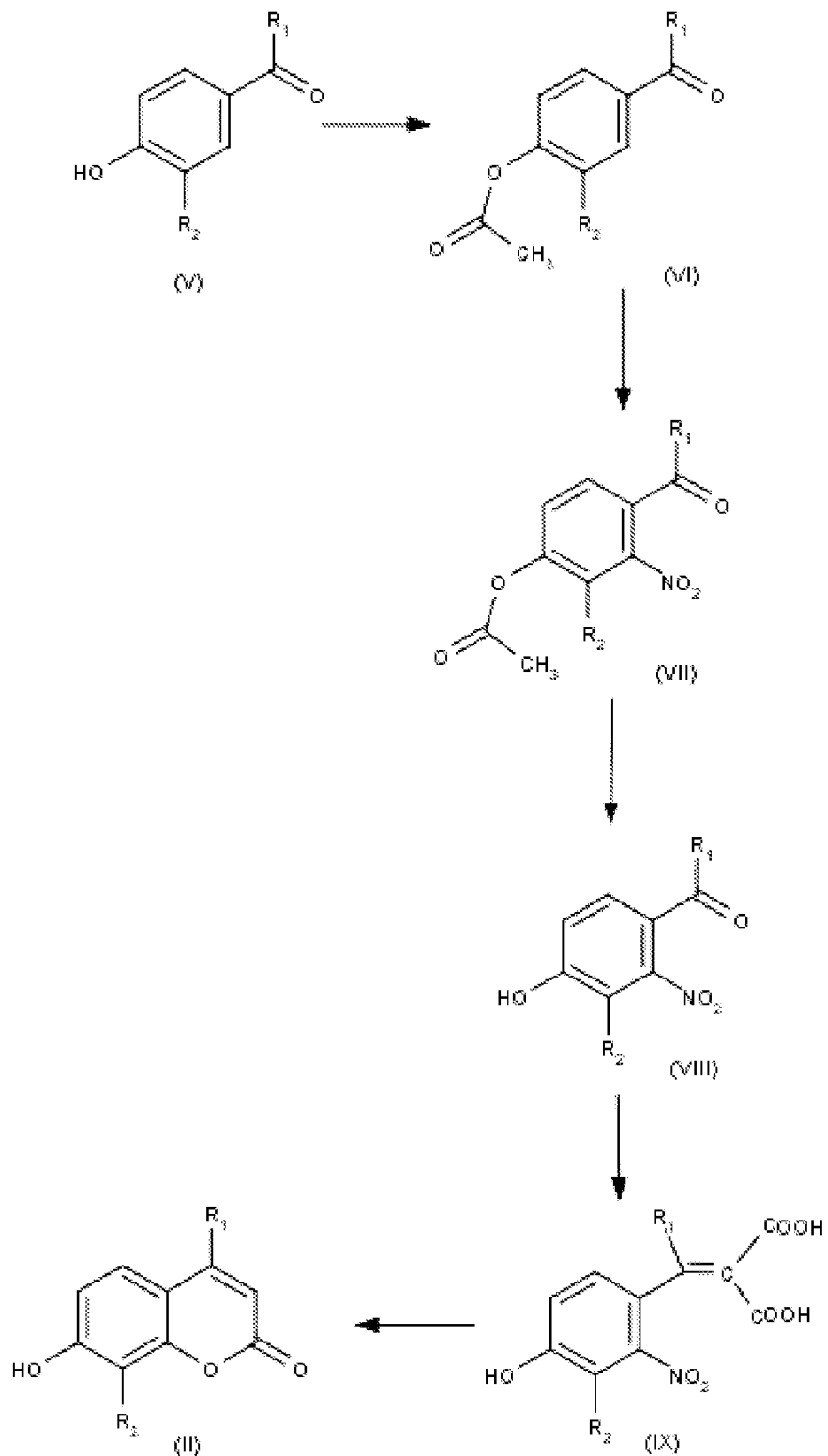
FIG. 2 is a diagram illustrating the synthesis of a compound of formula (II) from a compound of formula (V).

(II)

wherein R₁ is selected from the group consisting of a hydrogen atom; a linear C1-C6 alkyl group; and a branched C1-C6 alkyl group, and wherein R₂ is selected from the group consisting of a hydrogen atom, a linear C1-C6 alkyl group, a branched C1-C6 alkyl group, a linear C1-C6 alkoxy group, and a branched C1-C6 alkoxy group. FIG. 2 is a diagram illustrating one embodiment of the present disclosure for the synthesis of a compound of formula (II).

In certain embodiments, step (a), the acetylation of the compound of formula (V), is carried out using acetic anhydride or acetyl chloride. In certain embodiments, acetylation is performed with acetic anhydride. This acetylation step (a) is advantageously conducted at ambient temperature in order to prevent the formation of degradation products.

In certain embodiments, the compound of formula (VI) obtained in step (a) undergoes nitration (step b). In certain embodiments, the nitration of the compound of formula (VI) is performed using concentrated nitric acid to form the compound of formula (VII). In certain embodiments, the concentrated nitric acid may be fuming nitric acid. This nitration step is generally performed cold, particularly at a temperature of from about 0° C. to about 5° C.

In certain embodiments, following the nitration step (b), the acetyl group of the compound of formula (VII) is eliminated by hydrolysis (step c). In certain embodiments, hydrolysis step (c) is performed in basic medium. In certain embodiments, the compound of formula (VII) may be treated with a strong base such as sodium hydroxide, and then may be neutralized with a strong acid such as hydrochloric acid, to form the compound of formula (VIII).

In certain embodiments, following the hydrolysis step (c), the compound of formula (VIII) then undergoes Knoevenagel condensation (step d), which is condensation between an aldehyde and an active methylene compound to form a C—C bond. In certain embodiments, the active methylene compound may be malonic acid or a derivative thereof. In certain embodiments, Knoevenagel condensation is performed using malonic acid. The Knoevenagel condensation is performed by heating the reaction mixture in acid medium. In order to prevent decarboxylation of the compound of formula (VIII), the Knoevenagel condensation is generally performed at a temperature of from about 50° C. to about 70° C., for a time of from about 70 hours to about 110 hours. In certain embodiments, Knoevenagel condensation is performed at about 60° C. for about 96 hours.

Following the Knoevenagel condensation step, step (e) of cyclizing the compound of formula (IX) is performed. Cyclizing the compound of formula (IX) comprises copper-catalyzed coupling. Cyclization is generally performed at high temperature. In certain embodiments, cyclization may be performed at a temperature greater than about 100° C. In certain embodiments, cyclization may be performed at a temperature of from about 120° C. to about 150° C. In certain embodiments, cyclization step (e) may comprise reducing the nitro group of the compound of formula (IX) to facilitate cyclization to form the compound of formula (II).

In certain embodiments, the present disclosure provides a method for the synthesis of a compound of the following formula (I):

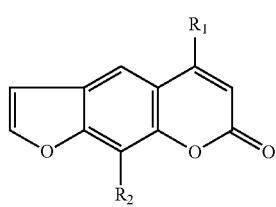

wherein $R_1$ is selected from the group consisting of a hydrogen atom; a linear C1-C6 alkyl group; and a branched C1-C6 alkyl group, and wherein $R_2$ is selected from the group consisting of a hydrogen atom, a linear C1-C6 alkyl group, a branched C1-C6 alkyl group, a linear C1-C6 alkoxy group, and a branched C1-C6 alkoxy group, and wherein the method comprises: (a) acetylating a compound of formula (II):

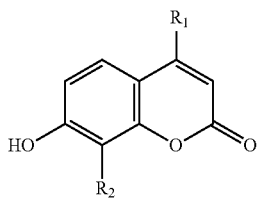

wherein $R_1$ and $R_2$ are as described above, wherein step (a) forms a compound having the following formula (III):

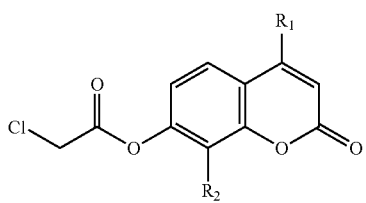

wherein $R_1$ and $R_2$ are as described above; (b) subjecting the compound of formula (III) as obtained from step (a) to a Fries rearrangement, wherein step (b) forms a compound having the following formula (IV):

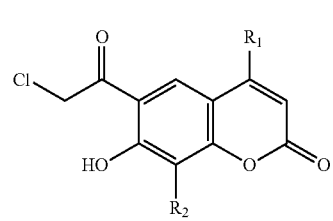

wherein $R_1$ and $R_2$ are as described above; and (c) cyclizing, reducing and aromatizing the compound of formula (IV) obtained from step (b) to form the compound of formula (I).

In one embodiment, the present disclosure provides a method comprising: (a) acetylating a compound having the following formula (II):

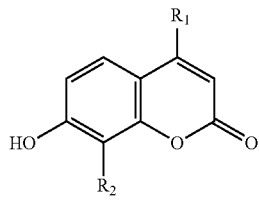

wherein acetylating the compound of formula (II) forms a compound having the following formula (III):

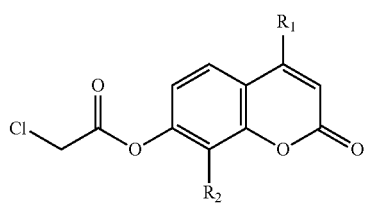

(b) subjecting the compound of formula (III) from step (a) to a Fries rearrangement, wherein the Fries rearrangement forms a compound having the following formula (IV):

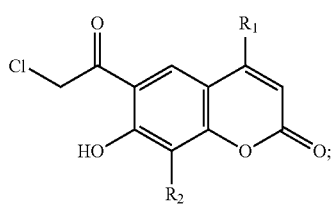

(c) subjecting the compound of formula (IV) obtained in step (b) to cyclization, reduction and aromatization, to form a compound having the following formula (I):

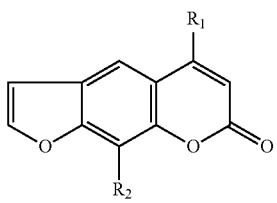

wherein $R_1$ in formulas (I)-(IV) is selected from the group consisting of a hydrogen atom; a linear C1-C6 alkyl group; and a branched C1-C6 alkyl group, and wherein $R_2$ in formulas (I)-(IV) is selected from the group consisting of a hydrogen atom; a linear C1-C6 alkyl group; a branched C1-C6 alkyl group; a linear C1-C6 alkoxy group; and a branched C1-C6 alkoxy group.

To facilitate a better understanding of the present disclosure, the following examples of certain aspects of some embodiments are given. In no way should the following examples be read to limit, or define, the entire scope of the invention.

EXAMPLES

Example 1

Synthesis of 8-MOP from Hydrangetin

1st Step: Acetylation (Obtaining Compound A)

1.8 g of hydrangetin (0.01 mole) is acetylated with 1.35 g of 2-chloroacetyl chloride (0.012 mole) by heating at 80° C. in dimethylformamide in the presence of sodium carbonate. After vacuum filtration and evaporation, 7-(2'-chloroacetyloxy)-8-methoxycoumarin (compound A) is isolated by crystallization in ethyl acetate (yield 90%).

2nd Step: Fries Rearrangement (Obtaining Compound B)

0.01 mole of 7-(2'-chloroacetyloxy)-8-methoxycoumarin (compound A) is directly heated in the presence of 0.015 mole aluminum chloride at 100° C. for 3 hours. After cooling and hydrolysis with diluted hydrochloric acid and ethyl acetate extraction, 6-(2'-chloroacetyl)-7-hydroxy-8-methoxycoumarin (compound B) is obtained after evaporation of the organic phase. The yield is 80%.

3rd Step: Cyclization of the Furan Ring and Reduction (Obtaining 8-MOP)

1.5 g of 6-(2'-chloroacetyl)-7-hydroxy-8-methoxycoumarin (0.006 mole) is cyclized by heating in 20 ml of acetone in the presence of 0.5 g sodium carbonate (0.007 mole), reducing using 1.4 mg of sodium borohydride (0.03 mole) and neutralizing in sulfuric acid medium. After vacuum filtration and evaporation and trituration in ethanol, 8-MOP is obtained (yield 80%). Lastly, the 8-MOP is recrystallized in ethanol.

The $^1$H NMR spectrum of 8-methoxysporalen (8-MOP) was performed in deuterated chloroform, according to the method of the European Pharmacopoeia 2.2.33. The assignment of resonance signals unambiguously confirms the structure of 8-methoxysporalen:

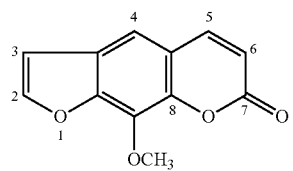

The $^1$H NMR spectrum of 8-methoxypsoralen (8-MOP) was performed on a Brücker apparatus (300 MHz) and the signal assignments are reported in the table below.

TABLE 1

Signal Assignments from $^1$H NMR spectrum of 8-methoxypsoralen

| δ (ppm)/TMS | multiplicity | integration | coupling constant | assignment |
|---|---|---|---|---|
| 4.1 | singlet | 3H | | OCH$_3$ |
| 6.4 | doublet | 1H | J = 9.5 Hz | H-6 |
| 7.1 | doublet | 1H | J = 2.1 Hz | H-2 |
| 7.7 | singlet | 1H | | H-4 |
| 8.1 | doublet | 2H | J = 9.5 Hz and J = 2.1 Hz | H-5 and H-3 |

The FTIR infrared spectrum of 8-methoxypsoralen was performed according to the method of the European Pharmacopoeia 2.2.24, on a Perkin Elmer spectrophotometer, between 650 cm$^{-1}$ and 4500 cm$^{-1}$.

Interpretation of the infrared absorption bands is presented in the table below.

TABLE 2

Infrared Adsorption Bands for FTIR Spectrum of 8-methoxypsoralen

| wave number ν (cm$^{-1}$) | function | vibration mode |
|---|---|---|
| 3120, 3060 | Aromatic CH | elongation |
| 2950 | Aliphatic CH | elongation |
| 1705 | C=O | elongation |
| 1620, 1590, 1550 | CH = Aromatic CH | elongation |
| 1215, 1180 | C—O—C | elongation |
| 870 | furan ring | elongation |

Example 2

Synthesis of Hydrangetin from Vanillin

Step 1: Acetylation to obtain 4-acetoxy-3-methoxybenzaldehyde (Compound 1)

28 ml (0.2 mole) of triethylamine and 220 mg (0.0018 mole) of 4-dimethylaminopyridine are added in drops to a solution of 20.0 g of vanillin (0.171 mole) and 26 ml acetic anhydride (0.275 mole) in 100 ml of dichloromethane, using a magnetic stirrer, by maintaining a temperature of less than 25° C. This reaction mixture is stirred for 30 min. at ambient temperature.

The organic phase is successively washed with 30 ml of water, with 40 ml of an aqueous hydrochloric acid solution 20% and lastly with 30 ml of a saturated aqueous solution of sodium chloride. After drying of the organic phase, the solution is vacuum evaporated. After cooling and adding cyclohexane, the product is isolated by vacuum filtration. The product is recrystallized in ethyl ether and 24.5 g of compound 1 is obtained (yield 75%).

Step 2: Nitration to obtain 4-acetoxy-3-methoxy-2nitrobenzaldehyde (Compound 2)

Small 12 g (0.06 mole) portions of compound 1 are slowly added to 50 ml of a fuming nitric acid solution cooled in an ice bath to 0° C. The reaction mixture is stirred for 1 hour at a temperature of less than 5° C. The reaction mixture is then poured into the ice water and stirred again for 1 hour. The product is isolated by vacuum filtration and cyclohexane washing (yield 80%-11.5 g).

Step 3: Hydrolysis and Obtaining 4-hydroxy-3-methoxy-2-nitrobenzaldehyde (Compound 3)

10 g of compound 2 (0.042 mole) are added to a solution of 40 ml of sodium hydroxide 33% (m/m). The reaction mixture is heated at reflux for 10 minutes. The reaction mixture is diluted with 40 ml of water and acidified with concentrated hydrochloric acid (HCl 6N) to neutral pH. After cooling, the product is precipitated and compound 3 is isolated by vacuum filtration and by several washings with water (yield 85%-7.2 g of compound 3).

Step 4: Preparation of (4-hydroxy-3-methoxy-2-nitrobenzylidene)malonic acid (Compound 4)

A mixture of 9.8 g of compound 3 (0.05 mole) and 6.8 g of malonic acid (0.065 mole) is heated in 15 ml of acetic acid at 60° C. for 96 hours. After vacuum evaporation, the product is crystallized after cooling and addition of dichloromethane, and then isolated by vacuum filtration. 13.0 g of compound 4 is obtained (yield 90%).

Step 5: Preparation of Hydrangetin

A mixture of 3.4 g of compound 4 (0.014 mole) and 360 mg of copper powder is heated to 130° C.-140° C. in 50 ml of quinoline for 5 min. After cooling, 120 ml of water and then 60 ml of concentrated hydrochloric acid (HCl 10N) are added. The aqueous phase is purified by extraction with 100 ml of dichloromethane to eliminate impurities, and then the product is extracted from the aqueous phase by a minimum of three extractions with 100 ml of ethyl acetate. After drying of the organic phase, it is vacuum evaporated and the product is crystallized in ethyl acetate. The product is finally recrystallized in ethyl acetate to obtain 2.1 g of hydrangetin (yield 78%).

The $^1$H NMR spectrum of hydrangetin was performed in deuterated dimethyl sulfoxide, according to the method of the European Pharmacopoeia 2.2.33. The assignment of resonance signals unambiguously confirms the structure of hydrangetin.

The $^1$H NMR spectrum of hydrangetin was performed on a Brücker apparatus (300 MHz) and the signal assignments are reported in the table below.

TABLE 3

Signal Assignments from $^1$H NMR spectrum of hydrangetin

| δ (ppm)/TMS | multiplicity | integration | assignment |
|---|---|---|---|
| 3.6 | singlet | 3H | OCH$_3$ |
| 7.1 | triplet | 2H | Aromatic H |
| 7.3 | doublet | 1H | Aromatic H |
| 11.1 | singlet | 1H | CH=O |

The FTIR infrared spectrum of hydrangetin was performed according to the method of the European Pharmacopoeia 2.2.24, on a Perkin Elmer spectrophotometer, between 650 cm$^{-1}$ and 4500 cm$^{-1}$. Interpretation of the infrared absorption bands is presented in the table below.

TABLE 4

Infrared Adsorption Bands for FTIR Spectrum of hydrangetin

| wave number ν (cm$^{-1}$) | function | vibration mode |
|---|---|---|
| 3296 | Phenolic OH | elongation |
| 3010 | Aromatic CH | elongation |
| 1727 | O—CO—CH$_3$ | elongation |
| 1692 | CH=CH | elongation |
| 1255 | OCH3 | elongation |

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
    (a) acetylating a compound having the following formula (II):

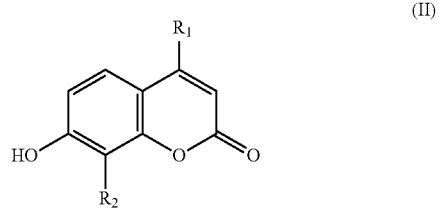

wherein acetylating the compound of formula (II) forms a compound having the following formula (III):

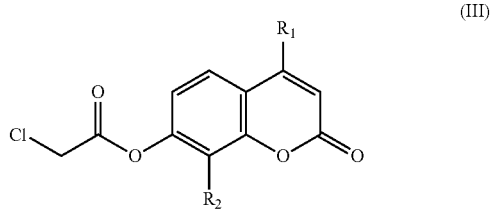

(b) subjecting the compound of formula (III) from step (a) to a Fries rearrangement performed at a temperature of 90° C. to 110° C., wherein the Fries rearrangement forms a compound having the following formula (IV):

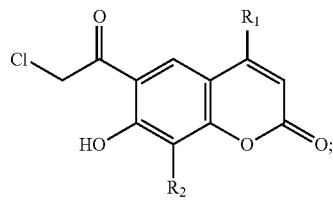

(IV)

(c) subjecting the compound of formula (IV) obtained in step (b) to cyclization, reduction and aromatization, to form a compound having the following formula (I):

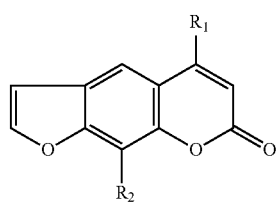

(I)

wherein R1 in formulas (I)-(IV) is selected from the group consisting of a hydrogen atom; a linear C1-C6 alkyl group; and a branched C1-C6 alkyl group, and wherein R2 in formulas (I)- (IV) is selected from the group consisting of a hydrogen atom; a linear C1-C6 alkyl group; a branched C1-C6 alkyl group; a linear C1-C6 alkoxy group; and a branched C1-C6 alkoxy group.

2. The method of claim 1, wherein R1 is a hydrogen atom.
3. The method of claim 1, wherein R2 is a methoxy group.
4. The method of claim 2, wherein R2 is a methoxy group.
5. The method of claim 1, wherein step (a) is performed using 2-chloroacetyl chloride in the presence of a base.
6. The method of claim 1, wherein the cyclization comprises heating the compound of formula (IV) in the presence of a base.
7. The method of claim 1, wherein the reduction is performed using an alkaline borohydride.
8. The method of claim 7, wherein the alkaline borohydride is sodium borohydride.
9. The method of claim 1, further comprising preparing a compound of formula (II) from a compound having the following formula (V):

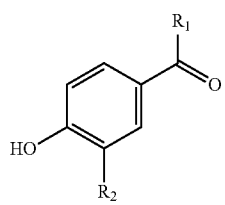

(V)

wherein R1 is selected from the group consisting of a hydrogen atom; a linear C1-C6 alkyl group; and a branched C1-C6 alkyl group, and wherein R2 is selected from the group consisting of a hydrogen atom; a linear C1-C6 alkyl group; a branched C1-C6 alkyl group; a linear C1-C6alkoxy group; and a branched C1-C6 alkoxy group.

10. The method of claim 1, wherein step (b) results in a yield of the compound of formula IV of at least about 80%.

11. The method of claim 9, wherein preparing the compound of formula (II) comprises:
(a) acetylating the compound of formula (V) to form a compound having the following formula (VI):

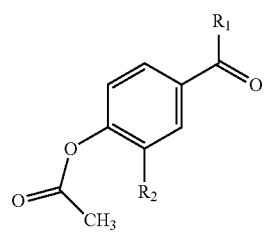

(VI)

(b) nitrating the compound of formula (VI) obtained in step (a) to form a compound having the following formula (VII):

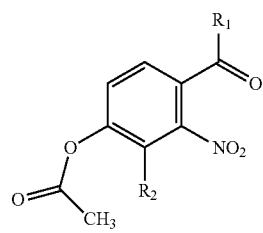

(VII)

(c) hydrolyzing the compound of formula (VII) obtained in step (b) to form a compound having the following formula (VIII):

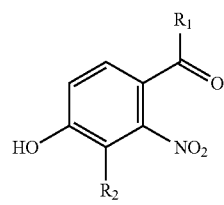

(VIII)

(d) subjecting the compound of formula (VIII) obtained in step (c) to Knoevenagel condensation, wherein the Knoevenagel condensation forms a compound having the following formula (IX):

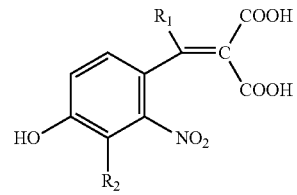

(IX)

(e) cyclizing the compound of formula (IX) obtained in step (d) to form the compound of formula (II), wherein R1 in formulas (VI)-(IX) is selected from the group consisting of a hydrogen atom; a linear C1-C6 alkyl group; and a branched C1-C6 alkyl group, and wherein R2 in formulas (VI)-(IX) is selected from the group consisting of a hydrogen atom; a linear C1-C6 alkyl group; a branched C1-C6 alkyl group; a linear C1-C6 alkoxy group; and a branched C1-C6 alkoxy group.

12. The method of claim 11, wherein step (a) is performed using acetic anhydride.

13. The method of claim 11, wherein step (b) is performed using concentrated nitric acid.

14. The method of claim 11, wherein step (c) is performed in basic medium.

15. The method of claim 11, wherein step (d) comprises heating the compound of formula (VIII) under acidic conditions.

16. The method of claim 11, wherein step (e) comprises copper-catalyzed coupling.

17. The method of claim 11, wherein the Knoevenagel condensation is performed at a temperature of from about 50° C. to about 70° C. for a time of from about 70 hours to about 110 hours.

18. The method of claim 11, wherein the Knoevenagel condensation is performed at about 60° C. for about 96 hours.

19. The method of claim 1, wherein step (c) results in a yield of the compound of formula (I) of at least about 80%.

* * * * *